US009788947B2

(12) United States Patent
Ruyra-Baliarda et al.

(10) Patent No.: US 9,788,947 B2
(45) Date of Patent: Oct. 17, 2017

(54) HEART VALVE SEWING CUFF

(71) Applicant: ON-X LIFE TECHNOLOGIES, INC., Austin, TX (US)

(72) Inventors: Francisco Javier Ruyra-Baliarda, Barcelona (ES); Josep Gatell Ferre, Barcelona (ES); Fletcher D. Southard, Austin, TX (US); Jack Bokros, Austin, TX (US); Elva Correa, Hutto, TX (US); Jeffery Poehlmann, Austin, TX (US)

(73) Assignee: On-X Life Technologies, Inc., Austin, TX (US)

( * ) Notice: Subject to any disclaimer, the term of this patent is extended or adjusted under 35 U.S.C. 154(b) by 0 days.

(21) Appl. No.: 15/131,371

(22) Filed: Apr. 18, 2016

(65) Prior Publication Data

US 2016/0270915 A1    Sep. 22, 2016

Related U.S. Application Data

(63) Continuation of application No. 14/118,656, filed as application No. PCT/US2012/039378 on May 24, 2012, now Pat. No. 9,314,333.
(Continued)

(51) Int. Cl.
*A61F 2/24*    (2006.01)
*A61B 17/04*    (2006.01)

(52) U.S. Cl.
CPC ........ *A61F 2/2445* (2013.01); *A61B 17/0482* (2013.01); *A61F 2/2409* (2013.01);
(Continued)

(58) Field of Classification Search
CPC .................................................... A61F 2/2403
See application file for complete search history.

(56) References Cited

U.S. PATENT DOCUMENTS 3,736,598 A    6/1973 Bellhouse et al.
4,259,753 A    4/1981 Liotta
(Continued)

FOREIGN PATENT DOCUMENTS

WO    99/34753    7/1999

OTHER PUBLICATIONS

PCT International Search Report issued in corresponding PCT/US2012/039378 dated Nov. 27, 2012 (6 pages).
(Continued)

*Primary Examiner* — Thomas J Sweet
*Assistant Examiner* — Wade P Schutte
(74) *Attorney, Agent, or Firm* — Trop, Pruner & Hu, P.C.

(57) ABSTRACT

An embodiment of the invention includes a sewing cuff for aortic heart valves that better approximates native anatomy by better mating with the crown-like anatomical annulus. Limiting distortion of the crown-like annulus provides better blood flow and overall valve function and provides a physician greater ease of implantation since native anatomy is not flattened. Thus, the surgeon may attach sutures to the fibrous tissue of the crown-like anatomical annulus without distorting the shape of the native anatomy. An embodiment includes a scalloped sewing cuff assembly (with semilunar arches) that tracks the crown-like annulus. Another embodiment provides a sewing cuff positioned over the majority of the valve's length, thus allowing the surgeon greater flexibility as to where he or she can attach sutures to the surgical annulus. Conventional valves, which are primarily "low-profile" devices, do not offer such ability. Other embodiments are described herein.

11 Claims, 5 Drawing Sheets

Related U.S. Application Data (60) Provisional application No. 61/636,045, filed on Apr. 20, 2012, provisional application No. 61/490,188, filed on May 26, 2011.

(52) U.S. Cl.
CPC ..... *A61F 2/2412* (2013.01); *A61F 2220/0008* (2013.01); *A61F 2230/0069* (2013.01); *A61F 2250/006* (2013.01)

(56) References Cited

U.S. PATENT DOCUMENTS

| | | | |
|---|---|---|---|
| 5,607,470 | A | 3/1997 | Milo |
| 6,068,657 | A | 5/2000 | Lapeyre et al. |
| 6,371,983 | B1 | 4/2002 | Lane |
| 6,383,147 | B1 | 5/2002 | Stobie |
| 6,716,244 | B2 | 4/2004 | Klaco |
| 6,790,229 | B1 * | 9/2004 | Berreklouw ........... A61B 17/11 606/153 |
| 6,951,573 | B1 | 10/2005 | Dilling |
| 7,641,687 | B2 | 1/2010 | Chinn et al. |
| 7,776,084 | B2 | 8/2010 | Johnson |
| 7,803,186 | B1 | 9/2010 | Li et al. |
| 2002/0173842 | A1 | 11/2002 | Buchnan |
| 2002/0183834 | A1 | 12/2002 | Klaco |
| 2003/0023302 | A1 | 1/2003 | Moe et al. |
| 2005/0043760 | A1 | 2/2005 | Fogarty et al. |
| 2005/0096739 | A1 | 5/2005 | Cao |
| 2006/0095125 | A1 | 5/2006 | Chinn et al. |
| 2006/0195185 | A1 * | 8/2006 | Lane ..................... A61F 2/2412 623/2.38 |
| 2006/0195186 | A1 | 8/2006 | Drews et al. |
| 2006/0259137 | A1 | 11/2006 | Artof |
| 2006/0293745 | A1 | 12/2006 | Carpentier et al. |
| 2007/0016285 | A1 | 1/2007 | Lane |
| 2007/0225801 | A1 | 9/2007 | Drews et al. |
| 2007/0265701 | A1 | 11/2007 | Gurskis et al. |
| 2009/0209982 | A1 | 8/2009 | Hoerstrup et al. |
| 2010/0168844 | A1 | 7/2010 | Toomes |

OTHER PUBLICATIONS

Nicoló Piazza et al., "Anatomy of the Aortic Valvar Complex and Its Implications for Transcatheter Implantation of the Aortic Valve," Circulation Cardiovascular Interventions, Journal of the American Heart Association, Aug. 2008, pp. 74-81.

Hans-Hinrich Sievers, "Prosthetic Aortic Valve Replacement," The Journal of Thoracic and Cardiovascular Surgery, May 2005, vol. 129, No. 5, pp. 961-965.

Mike Poullis, "Stentless Aortic Valve Replacement Operation," retrieved from http://www.mpoullis.net/aodvd1/procs/Root/sv.htm; May 2011.

European Search Report, "Communication and Supplementary European Search Report," dated Dec. 23, 2014, in application No. 12789337.8-1662/2713955 PCT/US2012039378, 6 pages.

European Patent Office, Second Office Action dated Jul. 12, 2017, in European Patent Application No. 12789337.8.

* cited by examiner

HEART VALVE SEWING CUFF

This application is a continuation of U.S. patent application Ser. No. 14/118,656, filed Nov. 19, 2013, which was the National Stage of International Application No. PCT/US2012/039378, filed on May 24, 2012, which claims priority to U.S. Provisional Patent Application No. 61/636,045, filed Apr. 20, 2012, and U.S. Provisional Patent Application No. 61/490,188, filed on May 26, 2011, the content of which is hereby incorporated by reference.

BACKGROUND

Figure 1:
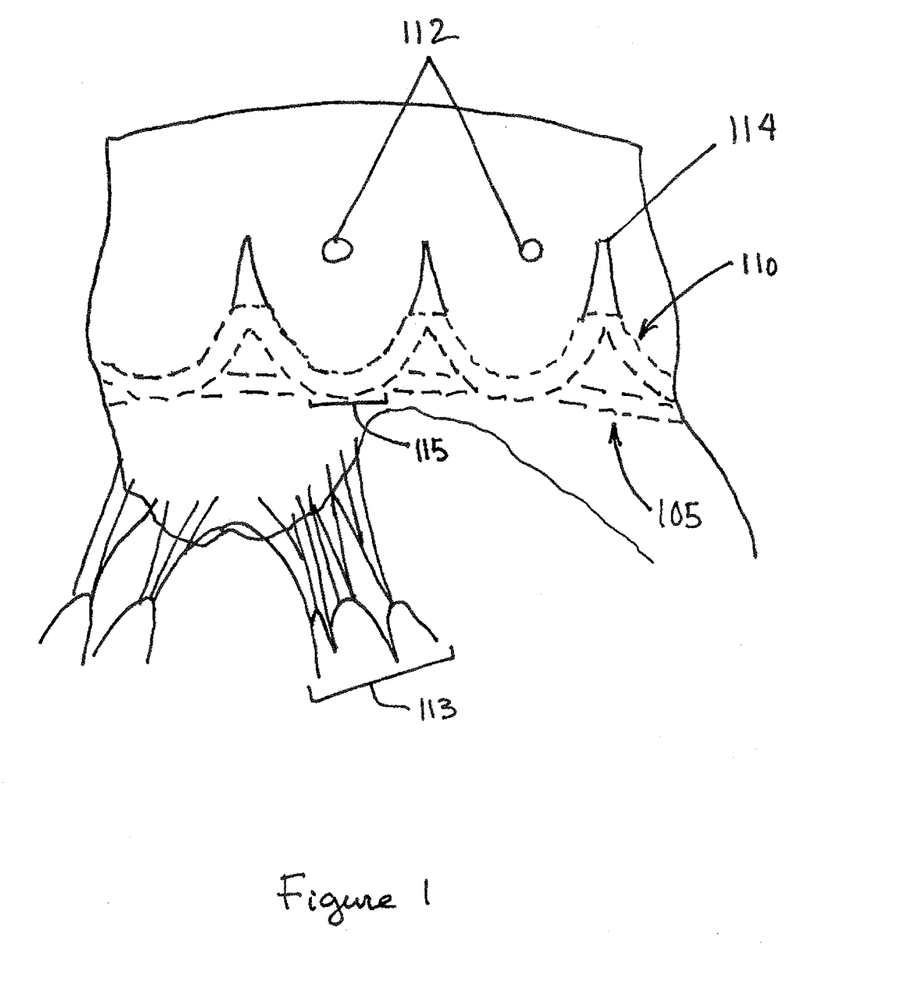
FIG. 1 depicts the aortic root.

As seen in FIG. 1 and addressed in *Prosthetic Aortic Valve Replacement* (Hans-Hinrich Seivers, Journal of Thoracic and Cardiovascular Surgery, 2005, Vol. 129: pp. 961-965), the aortic root includes segments of an ellipse where valve cusps are attached to the wall of the aorta and are supported by thickened, dense fibrous tissue. These fibrous thickenings form an "anatomic annulus" that has a crown-shaped configuration. In FIG. 1 this crown is depicted by the undulating dashed line of element 110. The three elliptical portions of the crown confine the sinuses on one side as the most proximal part of the aorta and the intervalvular trigones on the other side, which at least hemodynamically belong to the left ventricle. The dense fibrous tissue of the "anatomic annulus" is strong and provides an anchor for suturing a prosthetic valve within the aortic root.

There is no solid continuous anatomic circular annulus or ring in which to place the anchoring sutures as a geometric exact counterpart for the perfectly circular sewing rings of conventional prostheses. A "basic annulus" (see dashed line of element 105 of FIG. 1) consists of the nadirs of the elliptical attachments of the cusps (see element 115 as an example of one such nadir), the septal muscle, the ventricular membranous septum, and the distal end of the aortomitral curtain, together termed sometimes the ventriculoarterial junction and defining the smallest cross-sectional area between the left ventricle and the aorta. As such, this "basic annulus" defines the width of the root as measured from the sizers and also the seating of the conventional circular prostheses because the prostheses are fixed with sutures through the nadirs of the annulus.

Figure 2:
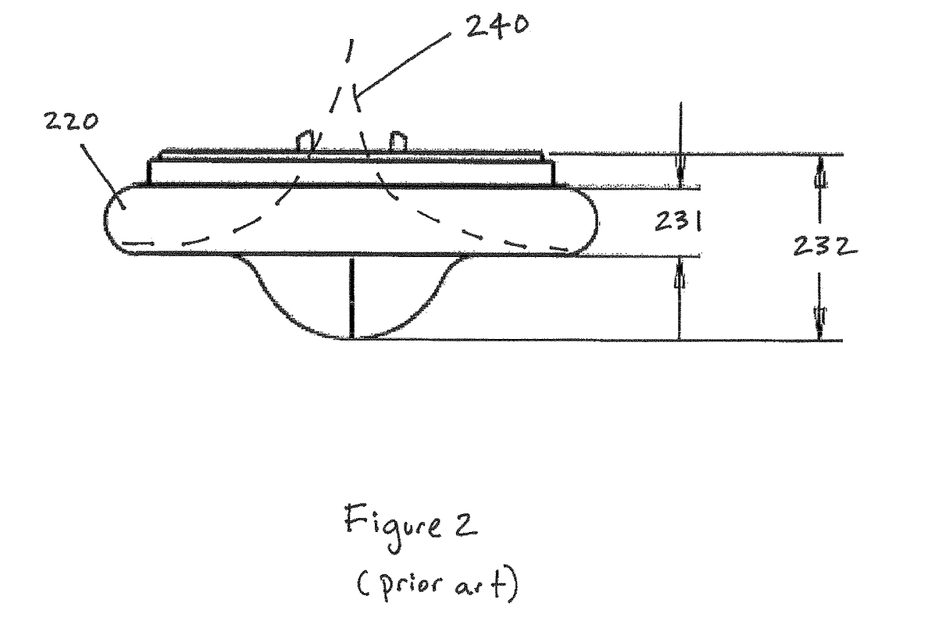
FIG. 2 depicts a conventional sewing cuff.

A conventional implant technique seats the prosthetic valve along annulus 105. The sewing ring of the valve is then sutured through the nadirs of the annulus. This restricts the surgeon to placing attachment sutures in roughly a two dimensional plane (i.e., along ring 105 with little vertical (i.e., superior/inferior) variance due to the narrow sewing ring 120). FIG. 2 includes a conventional device with a narrow sewing ring 220. The attachment feature of the ring, namely section 231, may be approximately 0.16 inches in height. This is approximately 38% of the entire height 232 (e.g., 0.44 inches) of the valve.

This two dimensional attachment methodology results in a general "flattening" of the annulus region. In other words, rings 110 and 105 are flattened together in some instances. Doing so may change the hemodynamic flow of blood upon entering/exiting the prosthetic valve. Specifically, when the surgeon seats the valve he or she must sew along line 105 of FIG. 1 because that is where the valve's sewing cuff lies. However, fibrous tissue is located along dotted line 110. To access the fibrous tissue (suitable for holding sutures) at line 110 the surgeon attaches sutures along dotted line 110 and then pulls the annulus up/down (i.e., lines 105 and 110 together) to get lines 105 and 110 in the same plane. As a result, the conventional attachment methodology and sewing rings generally "flatten" the annulus region.

BRIEF DESCRIPTION OF THE DRAWINGS

Features and advantages of embodiments of the present invention will become apparent from the appended claims, the following detailed description of one or more example embodiments, and the corresponding figures, in which:

DETAILED DESCRIPTION

In the following description, numerous specific details are set forth. However, it is understood that embodiments of the invention may be practiced without these specific details. Well-known structures and techniques have not been shown in detail to avoid obscuring an understanding of this description. References to "one embodiment", "an embodiment", "example embodiment", "various embodiments" and the like indicate the embodiment(s) so described may include particular features, structures, or characteristics, but not every embodiment necessarily includes the particular features, structures, or characteristics. Further, some embodiments may have some, all, or none of the features described for other embodiments. Also, as used herein "first", "second", "third" describe a common object and indicate that different instances of like objects are being referred to. Such adjectives are not intended to imply the objects so described must be in a given sequence, either temporally, spatially, in ranking, or in any other manner. Also, the terms "coupled" and "connected," along with their derivatives, may be used. In particular embodiments, "connected" may be used to indicate that two or more elements are in direct physical or electrical contact with each other and "coupled" may mean that two or more elements co-operate or interact with each other, but they may or may not be in direct physical or electrical contact. Also, while similar or same numbers may be used to designate same or similar parts in different figures, doing so does not mean all figures including similar or same numbers constitute a single or same embodiment.

An embodiment of the invention includes a sewing cuff for aortic heart valves that better approximates native anatomy by better mating with the crown-like anatomical annulus. Limiting distortion of the crown-like annulus provides better blood flow and overall valve function and provides a physician greater ease of implantation since native anatomy is not flattened. Thus, the surgeon may attach sutures to the fibrous tissue of the crown-like anatomical annulus without distorting the shape of the native anatomy. An embodiment includes a scalloped sewing cuff assembly (with semilunar arches) that tracks the crown-like annulus. Another embodiment provides a sewing cuff positioned over the majority of the valve's length, thus allowing the surgeon greater flexibility as to where he or she can attach sutures to the surgical annulus. Conventional valves, which are primarily "low-profile" devices, do not offer such ability. Other embodiments are described herein.

Figure 3:
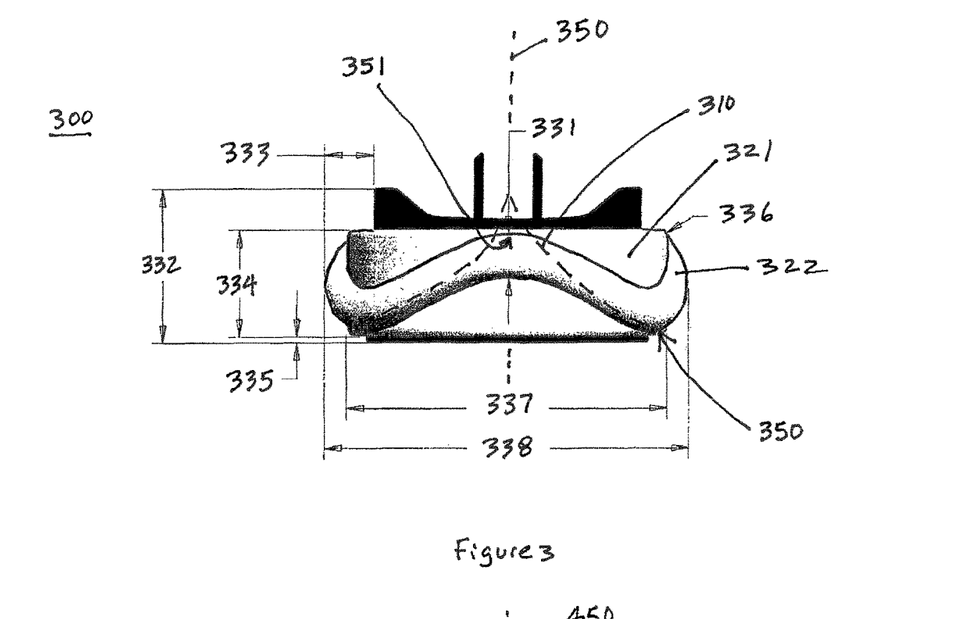
FIG. 3 includes an embodiment of the invention having first and second sewing cuffs.

FIG. 3 includes an embodiment of the invention having first and second sewing cuffs. Prosthetic heart valve 300 comprises a tubular valve body having longitudinal axis 350, an outlet end (top end of device of FIG. 3 which is the "downstream" end of the device), an inlet end (bottom end of device of FIG. 3 which is the "upstream" end of the device), an inner surface, and an outer surface. The outer surface comprises first sewing cuff 321 and second sewing cuff 322, both located entirely between the inlet and outlet ends (i.e., up to/equal to but not beyond the ends). In other embodiments one or more of the cuffs may not be located entirely between the inlets and outlet ends. For example, a portion of cuff 322 (and/or cuff 321) may extend further up (past any other portion of the device and past the outlet end) to trace the entire fibrous arch of the anatomical crown-like annulus.

In FIG. 3 two leaflets are shown (in their open position) within the tubular valve body. The leaflets intermittently and reversibly seal across the valve body inner surface to allow unidirectional flow (i.e., substantially unidirectional flow but not necessarily absolute unidirectional flow) through the tubular valve body from the inlet end to the outlet end. Embodiments are not limited to any single number of leaflets.

First cuff 321 includes a first height 334, and a first thickness (determined by subtracting the thickness of second cuff 322 from dimension 333) and a first outermost diameter 337. Second cuff 322 includes a second thickness (determined by subtracting dimension 337 from dimension 338 and dividing by two) and a second outermost diameter 338. Second cuff 322 includes one or more undulations comprising an apex (element 351 is an example of one or more apexes (a peak of an undulation) that may be included in cuff 322) adjacent a nadir (nadir 350 is a "trough" of the undulation that is "adjacent" apex 351 as there are no other nadirs or apexes between the two). Second sewing cuff 322 includes a second height, which is a vertical distance extending from the apex (highest point of cuff 322) to the nadir (lowest point of cuff 322).

Thus, valve 300 includes cuff 322 with semi-lunar arches shaped to allow the surgeon to deploy attachment sutures three dimensionally (i.e., with more vertical variance than found with narrow sewing cuff of FIG. 2) for improved device implantation. For example, the sutures may be placed along semi-lunar arches of cuff 322, which generally trace the anatomical crown-like annulus 110. Annulus 310 in FIG. 3 (analogous to annulus 110 of FIG. 1) is shown extending just beyond apex 351 but other embodiments may extend cuff 322 to extend as far as annulus 310. Valve 300 allows the surgeon to place sutures along cuff 322 and along annulus 310. This contrasts with traditional "two dimensional" sewing cuffs that restrict placement to a thin two dimensional plane of attachment (ring 105 of FIG. 1), thus, "flattening" the native annulus.

As used herein, "two dimensional" is not to be taken literally. A "two dimensional" ring (FIG. 2 element 220) obviously has three dimensions. However, the "two dimensional" nomenclature is used herein to indicate the thin dimension (lack of height) of the conventional ring (sewing ring and sewing cuff are used interchangeably herein).

In an embodiment first cuff 321 "passes through" second cuff 322. The outer perimeter of cuff 321 is thereby included within the inner diameter of cuff 322.

Figure 5:
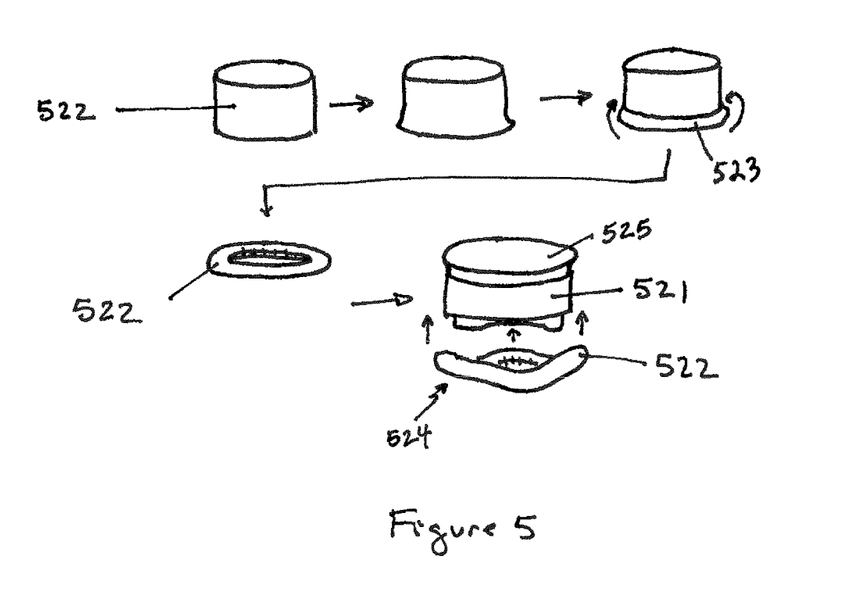
FIG. 5 includes a method of making an embodiment of the invention.

The embodiment of FIG. 3 includes embodiments wherein cuffs 321, 322 are formed from two pieces or one piece of material. For example, cuffs 321, 322 may comprise two pieces of fabric. As seen in FIG. 5, via a multistep process an embodiment is created. First, a short length of fabric (e.g., Polytetrafluoroethylene (PTFE)) 522 is provided. Second, one end of the fabric is rolled onto itself on the outside to yield a torroid 523. Then the rolled tube is stitched so it will not unravel. Afterwards the rolled tube may be pressed using dies to achieve a scalloped shape 524. The scalloped shape roll may then be slipped over cuff 521 (which may be a straight-walled thin inner sewing cuff installed on a valve 525). Cuff 522 may then be stitched to cuff 521.

In an embodiment a "filler", such as PTFE felt, may be rolled up inside cuff 522 to add bulk to the sewing cuff. In an embodiment, the filler may be a polyester fabric or Dacron®, which can be heat set to hold the undulating pattern. The filler may be a material such as titanium, shape memory nitonol, ultra high molecular weight polyethylene (UHMW), and the like. The filler may be rolled inside the outer cuff during fabrication and then deformed into a scalloped shape using a press, heat press, and the like to deform or shape the former. With memory materials such as nitinol, the scalloped cuff could be pre-deformed into the former, flattened for assembly with inner cuff 321, and then returned to its desired undulating shape.

In an embodiment the scalloped cuff 322 is not limited to being formed from a rolled tube. For example, cuff 322 could be a piece of PTFE braided chord with a round or oval (flattened) cross-section. This chord could be sewn or otherwise adhered (e.g., via adhesive) to cuff 321 (e.g., a straight walled inner sewing cuff).

Figure 6:
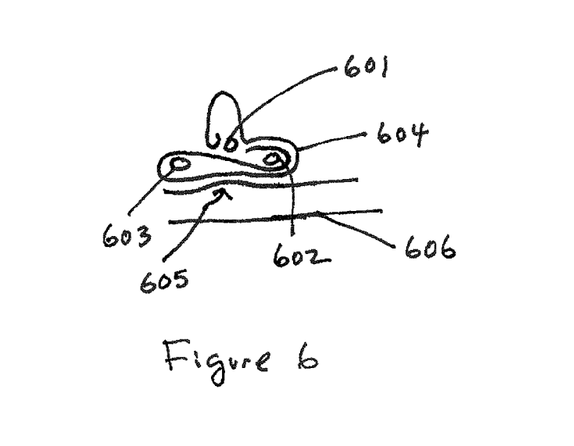
FIG. 6 includes a method of making an embodiment of the invention.

In another embodiment, cuffs 321, 322 may comprise a shared single piece of fabric or porous material (e.g., ePTFE). As seen in FIG. 6, a single piece of fabric 604 may be wound about elements 602, 603 thereby defining the upper and lower ends of inner cuff 321. Elements 602, 603 help the cuff maintain its shape and not slide or slip past or over projection 605 of valve 606. The same fabric 604 may be wound about former 601 (e.g., nitonol former) to create the outer cuff 322. Such an embodiment may be considered as having first and second cuffs that are monolithic with one another (in contrast to FIG. 5 having stitched together, non-monolithic cuffs).

In one embodiment the first and second cuffs both comprise fibrous materials (e.g., materials composed of fibers such as polyester). Both of cuffs 321, 322 may be composed of the same material but in other embodiments they may include differing materials. Thus, both cuffs (not just one cuff) are suitable for stitching and accepting needles and sutures. Thus, while preferably a surgeon may stitch along cuff 322 he or she may also/instead stitch at any point along cuff 321. This allows for variations in anatomic features (such as spacing between fibrous branches of the crown-like annulus, as further explained below).

Figure 4:
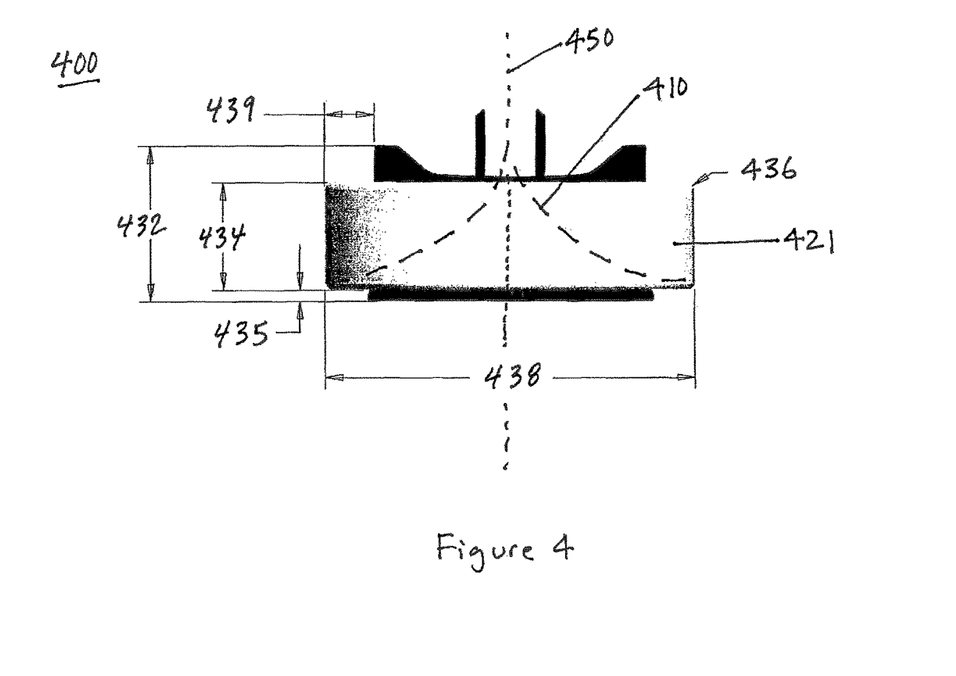
FIG. 4 includes an embodiment of the invention having a first sewing cuff.

FIG. 4 includes an embodiment of the invention disclosing a cuff with an extended height or vertical distance as compared to previous rings (e.g., FIG. 2). The extended height allows the surgeon to deploy attachment sutures three dimensionally (i.e., with vertical variance) for improved implantation.

FIG. 4 includes an embodiment having first cuff 421. Prosthetic heart valve 400 comprises a tubular valve body having longitudinal axis 450, an outlet end (top end of device of FIG. 4 which is the "downstream" end of the device), an inlet end (bottom end of device of FIG. 4 which is the "upstream" end of the device), an inner surface, and an outer surface. The outer surface comprises first sewing cuff 421 located entirely between the inlet and outlet ends. In other embodiments the cuff may not be located entirely between the inlet and outlet ends. In FIG. 4 two leaflets are shown (in their open position) within the tubular valve body but other numbers of leaflets are possible in other embodiments (as are other types of valve closing mechanisms). First cuff 421 includes a first height 434, a first thickness 439 and a first outermost diameter 438.

The embodiment of FIG. 4 allows great latitude to a user to suture cuff 421 along crown-like annulus ring 410, regardless of the variances of annulus 410 from patient to patient (and even among the leaflets within a single patient). Regarding variance among leaflets, as noted in *Anatomy of the Aortic Valvar Complex and Its Implications for Transcatheter Implantation of the Aortic Valve* (Piazza et al., Circulation Cardiovascular Interventions, 2008, Vol. 1, pp. 74-81), variations exist among individuals in the dimensions of the aortic root and in the same individual marked variations can exist in all aspects of the dimensions of the individual leaflets, including the height, width, surface area, and volume of each of the supporting sinuses of Valsalva. Regarding absolute width of each leaflet expressed as a percentage of the width of adjacent leaflets, comparisons of the right coronary and left coronary leaflets, noncoronary and right coronary leaflets, and left coronary and noncoronary leaflets varied between 76% and 159%, 62% and 162%, and 62% and 150%, respectively. When the height of each individual leaflet was expressed as a percentage of its width, the right coronary, noncoronary, and left coronary leaflets varied between 39% and 82%, 34% and 87%, and 34% and 113%, respectively.

While the embodiment of FIG. 4 is especially equipped to handle variances in ring 110, such an embodiment is also able to accommodate other suture preferences that may not necessarily track ring 110 due to the broadness of the cuff. In other words, cuff 421 provides a broad expanse for the surgeon to stitch wherever he or she desires.

For that matter, the embodiment of FIG. 3 is also accommodating. For instance, cuff 321 still contains a portion with height 334 that could be used for suturing if the semi-lunar raised surfaces of cuff 322 do not accommodate the desired suture pattern. This height 334 is still greater than the maximum height of conventional cuffs, such as height 231 in FIG. 2 (e.g., 0.39 inches vs. 0.16 inches). Thus, cuff 321 provides a broad expanse for the surgeon to stitch wherever he or she desires in addition to or instead of cuff 322.

Regarding dimensions, the conventional device of FIG. 2 includes dimensions 231 (e.g., 0.16 inches) and 232 (e.g., 0.44 inches). In contrast, FIG. 3 includes an embodiment having dimensions 333 (e.g., 0.18 inches), 331 (e.g., 0.16 inches), 336 (e.g., 4×0.03 inches, meaning the radius of curvature for the left and right bottom and top corners as seen in FIG. 3 have 0.03 inch radii of curvature), 337 (e.g., 1.18 inches), 338 (e.g., 1.34 inches), 335 (0.022 inches), 334 (e.g., 0.39 inches), 332 (e.g., 0.56 inches). The embodiment of FIG. 4 includes dimensions 439 (e.g., 0.18 inches), 436 (e.g., 4×0.03 inches), 438 (e.g., 1.34 inches), 435 (e.g., 0.039 inches), 434 (e.g., 0.39 inches), and 432 (e.g., 60 inches).

Also, while not shown, embodiments similar to FIG. 3 may include a semilunar raised service that has a greater dimension 331 than that of FIG. 3 (e.g., greater than 0.16 inches). As shown in FIG. 3, the height 334 may be about 0.39 inches and dimension 331 may be about 0.16 inches. Thus, 0.39−0.16=0.23 of cuff height not occupied by the semilunar surface of cuff 322. In an embodiment with a broader (greater height) raised semilunar surface, the overall cuff may remain at 0.39 in height but the semilunar surface height may grow to, for example, 0.30 leaving 0.09 of cuff height not occupied by the semilunar surface. This may result in a somewhat flatter semilunar surface angle of curvature. In other embodiments, the cuff height may be increased from 0.39 to a larger value such as, for example, 0.50 or beyond with care to provide clearance for coronary vessels and other anatomical features that cannot be covered by a prosthetic. Cutouts or voids may be included in a cuff to avoid such an anatomical feature. This may keep the angle of curvature in a broader semilunar surface consistent with that shown in FIG. 3, despite the curved surface being broader than 0.16 in height.

Thus, for the embodiment of FIG. 3 apex 351 includes a top and a bottom and a distance between the top and the bottom (331) is less than 0.2 inches. Also, height 334 is greater than 0.3 inches and may be 0.4, 0.5, or 0.6 inches. Further, total valve height extends from the inlet end to the outlet end (332) and height 334 is greater than 60% of the total valve height (332). In other embodiments, the percentage may differ and include, for example, 50, 55, 65, 70, 75, 80, 85, 90% and the like. In varying embodiments, the height from the top of an apex to the bottom of a nadir may less than, equal to, or more than height 334. In one embodiment, the apex includes a distance (331) between a top and bottom of the apex. That distance (331) is greater than 40% of height 332. However, in other embodiments that percentage may be 30, 35, 45, 50, 55, 65, 70, 75, 80, 85, 90% and the like. In an embodiment height 334 is greater than the height from the bottom of nadir 350 to the top of apex 351. In that same embodiment outermost diameter 337 is less than outermost diameter 338. In that same embodiment, the thickness of cuff 321 is less than the thickness of cuff 322.

While specific dimensions are mentioned herein those are just examples. Other dimensions and sizes are within the scope of inventive embodiments. Furthermore, valves may come in varying sizes with cuff(s) that increase/decrease in size accordingly. Kits may be provided including variably sized valves.

In an embodiment, the semilunar surfaces (a space between two adjacent apexes) are not equally distributed about the cuff. For example, to account for cases where a patient's leaflets have varying widths, a valve with three semilunar surfaces may have one of the three surfaces a different length (horizontal) than one or both of the other two semilunar surfaces. Thus, the user may rotate the valve to situate the longest semilunar surface (e.g., horizontal distance between troughs or endpoints of semilunar arch) adjacent the longest portion of annulus 310. However, in other embodiments the semilunar surfaces are equally distributed about the cuff. Thus, in one embodiment a first horizontal distance (reaching between an adjacent apex and nadir) is unequal to a second horizontal distance (reaching between another adjacent apex nadir couple) so that the undulations are unequally distributed about cuff 322.

In an embodiment, a valve with varying rings may be provided in a kit. The user may select from the rings once she or he has inspected the patient's anatomy. The rings may have varying arrangements of semilunar surfaces as described above. In various embodiments, the sewing cuffs include polyester (e.g., Dacron), polytetrafluoroethylene (e.g., Teflon), and/or other suitable materials.

Some embodiments, such as one similar to FIG. 4, may include a visible marker along the cuff (even though no cuff such as cuff 322 exists) to provide visual guidance for stitching a cuff along the path of annulus 110.

Figure 8:
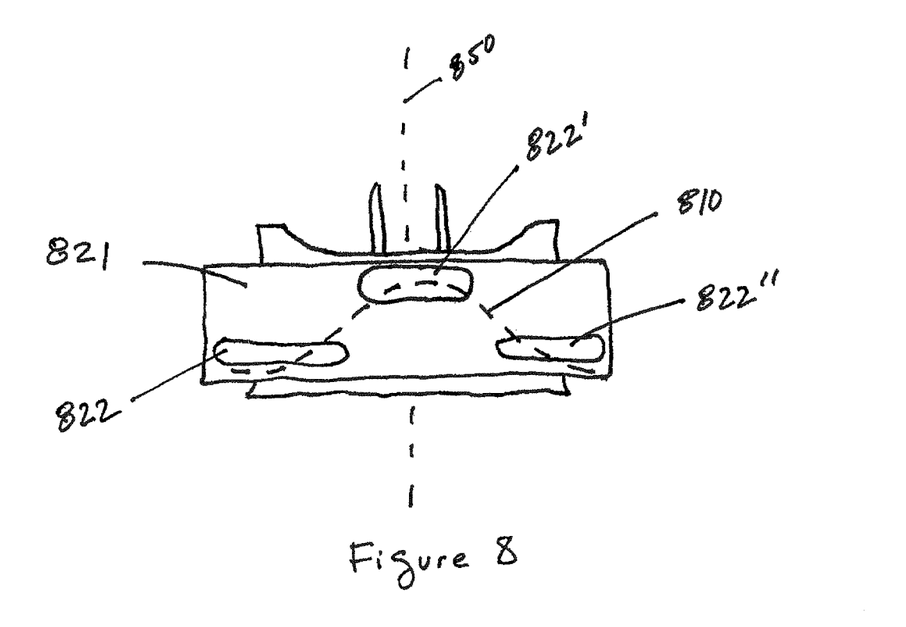
FIG. 8 includes an embodiment of the invention.

Also, embodiments describing an "undulating" cuff have been discussed above with regard to FIG. 3, cuff 322. However, an undulating cuff does not necessarily have to be contiguous. For example, FIG. 8 includes portions 822, 822', 822" that collectively provide an undulating cuff despite the portions failing to directly connect with each other and instead indirectly coupling to one another via cuff 821. Further, undulations needs not be smooth (similar to a sine wave) and instead may resemble a triangular wave, square wave, and the like.

Also, the cuffs of embodiments in FIGS. 3 and FIG. 4 are depicted as being smooth but other embodiments are not so limited and may include bumps, ridges, and the like. Cuff embodiments may include a vertical ridges, ridges set at an angle (e.g., 45 degrees), and/or horizontal ridges or bands (e.g., 2, 3 or 4 ridges that circumscribe the cuff). The valve may be a bioprosthetic including various portions of donor tissue (e.g., porcine tissue) and the like. Also valves are not only aortic but may be suitable for mitrel valves and the like.

In one embodiment a prosthetic heart valve comprises a tubular valve body having a longitudinal axis, an outlet end, an inlet end, an inner surface, and an outer surface, the outer surface comprising a first sewing cuff; wherein the first cuff includes a first height, and a first thickness and a first outermost diameter both taken orthogonal to the longitudinal axis. The tubular valve body may include a second sewing cuff that includes a second thickness and a second outermost diameter, both orthogonal to the longitudinal axis. The second cuff does not necessarily circumscribe the entire first cuff but may instead be a projection from the first sewing cuff. For example, in an embodiment similar to FIG. 8 (including 822' but not 822 or 822") cuff 822' projects away from first cuff 821 in a direction non-parallel to longitudinal axis 850. Both cuff 821 and 822' are configured to receive sutures so that, based on the patient anatomy, the surgeon may stitch the valve to the patient at cuff 822' and/or any location on cuff 821.

Various embodiments of the invention are suitable for implantation intra-annularly, intrasupra-annularly, and supra-annularly. For example, the embodiment of FIG. 4 may be implanted intra-annularly, intrasupra-annularly, and supra-annularly.

An embodiment of the invention includes a method including situating a mechanical valve, having a sewing cuff, in a patient's aortic root and suturing the cuff along the surgical annulus (110 of FIG. 1) while limiting or avoiding flattening of surgical annulus 110 and also taking into account anatomical variances of the fibrous portions of the heart and/or other anatomical issues. The cuff may be sutured along the thickened fibrous portions (see lines 110, 310, 410 for various examples) of the patient's fibrous crown-shaped annulus.

Figure 7:
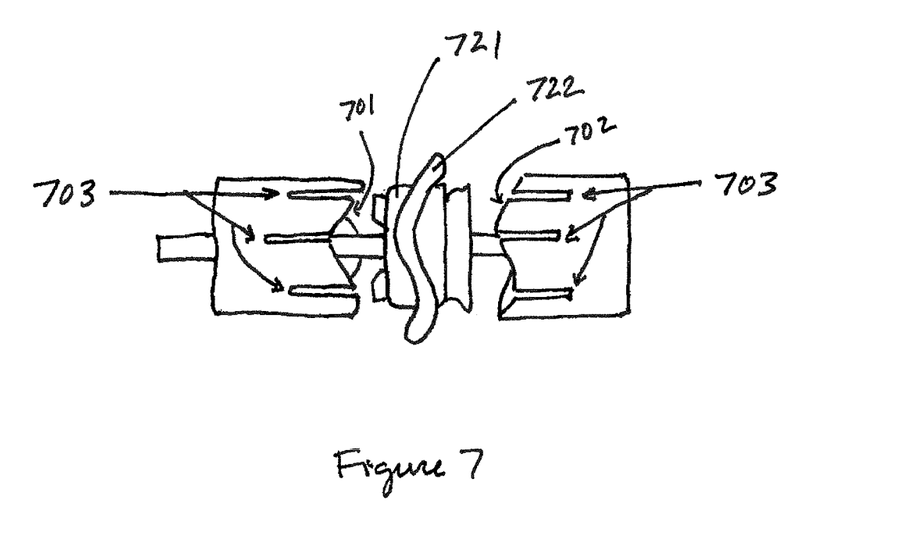
FIG. 7 includes a method of making an embodiment of the invention.

An embodiment includes a method of manufacturing a cuff. For example, FIG. 7 depicts a two piece mandrel with mating scalloped surfaces 701, 702. The two pieces slide coaxially on a center rod passing through the open leaflets of the valve. The two parts of the mandrel, when brought together, squeeze the base of the protruding portions of sewing cuff 722 into shape and hold it for stitching and coupling it to cuff 721. Narrow slits 703 in each mandrel half allow a curved needle to pass through sewing cuffs 721, 722 to secure them together. The stitches may be temporary or permanent. The method of FIG. 7 may work with the embodiment of FIG. 6. However, the method of FIG. 7 may also work with two piece embodiments (e.g., sew a separate sewing cuff flange onto a valve for a two piece cuff configuration such as FIG. 5).

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:
1. A prosthetic heart valve comprising:
a tubular valve body having a vertical axis, an outlet end, and an inlet end;
a sewing cuff located entirely between the inlet and outlet ends; and
at least one leaflet to intermittently allow flow through the tubular valve body from the inlet end to the outlet end;
wherein the sewing cuff includes a first portion comprising: (a)(i) first height that is uniform along an upper edge of the first portion, and (a)(ii) a first outermost diameter taken orthogonal to the vertical axis;
wherein the sewing cuff includes a second portion comprising: (b)(i) undulations that each comprise an apex adjacent a nadir, (b)(ii) a second height extending from a top of the apex to a bottom of the nadir, and (b)(iii) a second outermost diameter taken orthogonal to the vertical axis;
wherein both of the first and second portions include polytetrafluoroethylene (PTFE) fabric;
wherein the second height is at least 75% of the first height;
wherein the second outermost diameter is greater than the first outermost diameter;
wherein the tubular valve body includes a projection that extends horizontally away from the vertical axis;
wherein a subportion of the first portion is above the projection and an additional subportion of the first portion is below the projection; and
wherein the projection, subportion, and additional subportion are oriented in relation to each other such that the projection resists the subportion and additional subportion from sliding off the tubular valve body.

2. The valve of claim 1, wherein the first portion includes a cylindrical portion.

3. The valve of claim 2, wherein the cylindrical portion includes a circular perimeter that defines the first outermost diameter.

4. The valve of claim 1, wherein the first and second portions share a single, monolithic portion of the PTFE fabric.

5. The valve of claim 1, wherein the apex is directly connected to the nadir.

6. The valve of claim 1, wherein the first and second portions are both configured to accept and retain sutures.

7. The valve of claim 1, wherein the first and second portions are non-monolithic with one another.

8. The valve of claim 1, wherein:
the second portion does not extend above the first portion;
the second portion does not extend below the first portion.

9. The valve of claim 1, wherein:
the first and second portions share a single, monolithic portion of the PTFE fabric;
a radial axis, radiating horizontally outward from and orthogonal to the vertical axis, intercepts the monolithic portion of the PTFE fabric at least 3times; and
the horizontal axis intercepts the projection.

10. The valve of claim 9, wherein an additional vertical axis intercepts the monolithic portion of the PTFE fabric at least 3times.

11. The valve of claim 1, wherein the prosthetic heart valve is not a bioprosthetic.

\* \* \* \* \*

UNITED STATES PATENT AND TRADEMARK OFFICE
CERTIFICATE OF CORRECTION

PATENT NO. : 9,788,947 B2
APPLICATION NO. : 15/131371
DATED : October 17, 2017
INVENTOR(S) : Francisco Javier Ruyra-Baliarda et al.

Page 1 of 1

It is certified that error appears in the above-identified patent and that said Letters Patent is hereby corrected as shown below:

In the Claims

Claim 9, Line 63, "of the PTFE fabric at least 3times" should be --of the PTFE fabric at least 3 times--.
Claim 10, Line 67, "least 3times" should be --least 3 times--.

Signed and Sealed this
Fifth Day of December, 2017

Joseph Matal
*Performing the Functions and Duties of the
Under Secretary of Commerce for Intellectual Property and
Director of the United States Patent and Trademark Office*